United States Patent
Yadav

(10) Patent No.: US 6,645,174 B1
(45) Date of Patent: Nov. 11, 2003

(54) STENT DELIVERY SYSTEM

(76) Inventor: Jay S. Yadav, 109 Waverly La., South Russell, OH (US) 44022

(*) Notice: Subject to any disclaimer, the term of this patent is extended or adjusted under 35 U.S.C. 154(b) by 0 days.

(21) Appl. No.: 09/806,654

(22) PCT Filed: Sep. 30, 1999

(86) PCT No.: PCT/US99/22561
§ 371 (c)(1),
(2), (4) Date: Mar. 29, 2001

(87) PCT Pub. No.: WO00/18342
PCT Pub. Date: Apr. 6, 2000

Related U.S. Application Data

(60) Provisional application No. 60/102,529, filed on Sep. 30, 1998.

(51) Int. Cl.[7] .......................... A61F 11/00; A61M 29/00
(52) U.S. Cl. .................................. 604/103.07; 623/1.11
(58) Field of Search ............................. 604/96.01, 103, 604/103.05, 103.06, 103.14, 103.07; 606/194, 198; 623/1.11

(56) References Cited

U.S. PATENT DOCUMENTS 5,643,279 A * 7/1997 Trotta ........................ 606/194
5,935,135 A * 8/1999 Bramfitt et al. ............ 623/1.11

* cited by examiner

Primary Examiner—Anhtuan T. Nguyen
(74) Attorney, Agent, or Firm—Reed Smith LLP

(57) ABSTRACT

A non-sheath balloon expandable stent delivery system (20) has a catheter-mounted balloon (25) whose ends (26, 27) are invaginated and folded over onto the balloon itself. Thus, when a stent (29) is mounted on the balloon, the balloon ends fold over the ends of the stent, thus covering its ends and serving a sheath function. The folded over ends (26A, 27A) could cover the terminal portions of the stent or could reach to the middle of the stent and cover the entire stent. When the balloon is inflated to deploy the stent; the balloon ends inflate and uncover the stent. The balloon inflation ports in the balloon catheter could be positioned so as to preferentially direct the inflating fluid into the balloon ends/invaginations (26A, 27A) to assure their inflation before the inflation of the body of the balloon. Because the stent will be crimped on the body of the balloon, the pressure and wall tension required to inflate the body of the balloon will be much greater than the pressure required to inflate the unrestricted balloon ends. The balloon ends will thus expand and move off the ends of the stent before the stent expands so as not to become trapped between the stent and an organ or corporeal vessel wall.

22 Claims, 2 Drawing Sheets

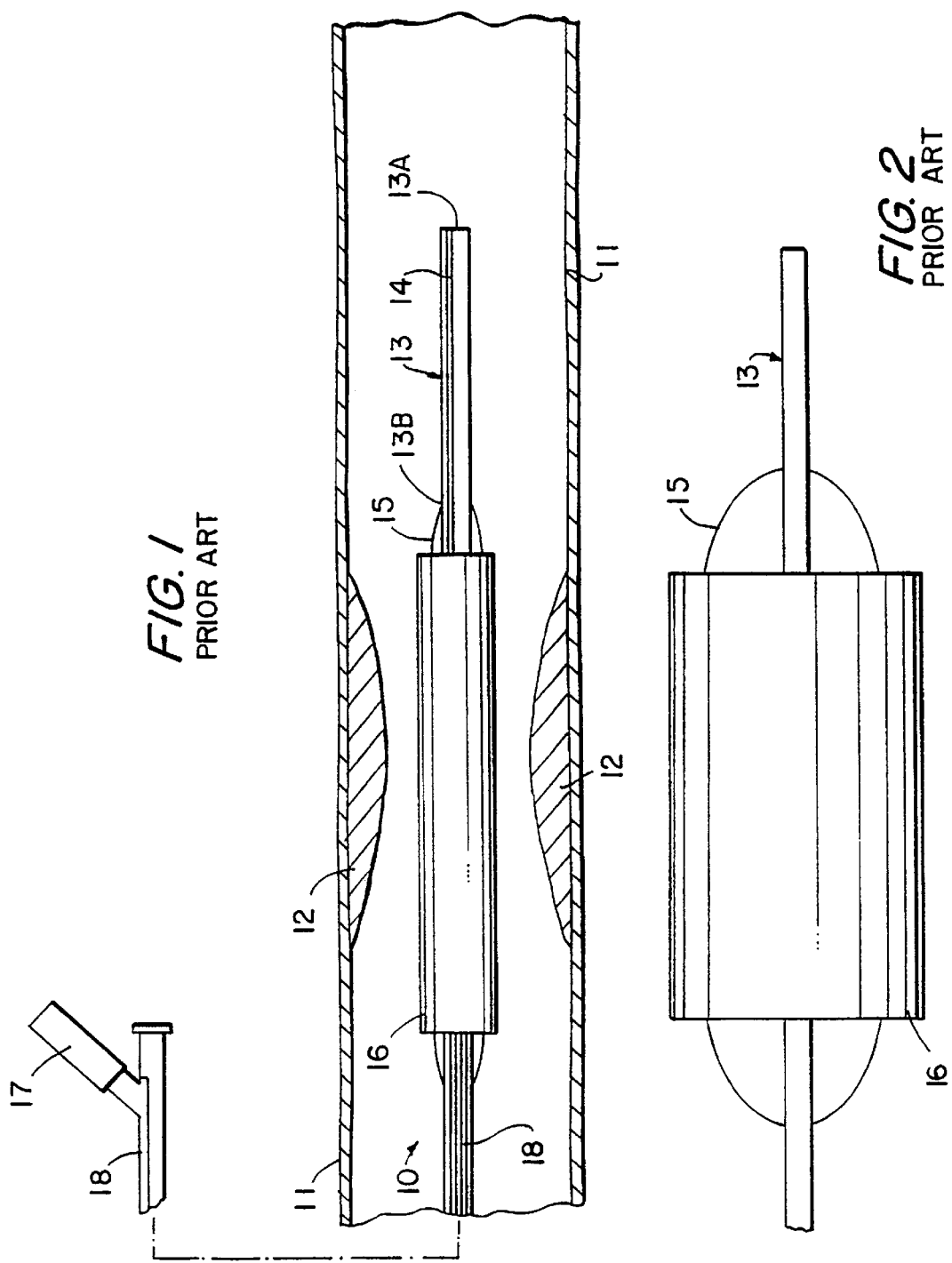

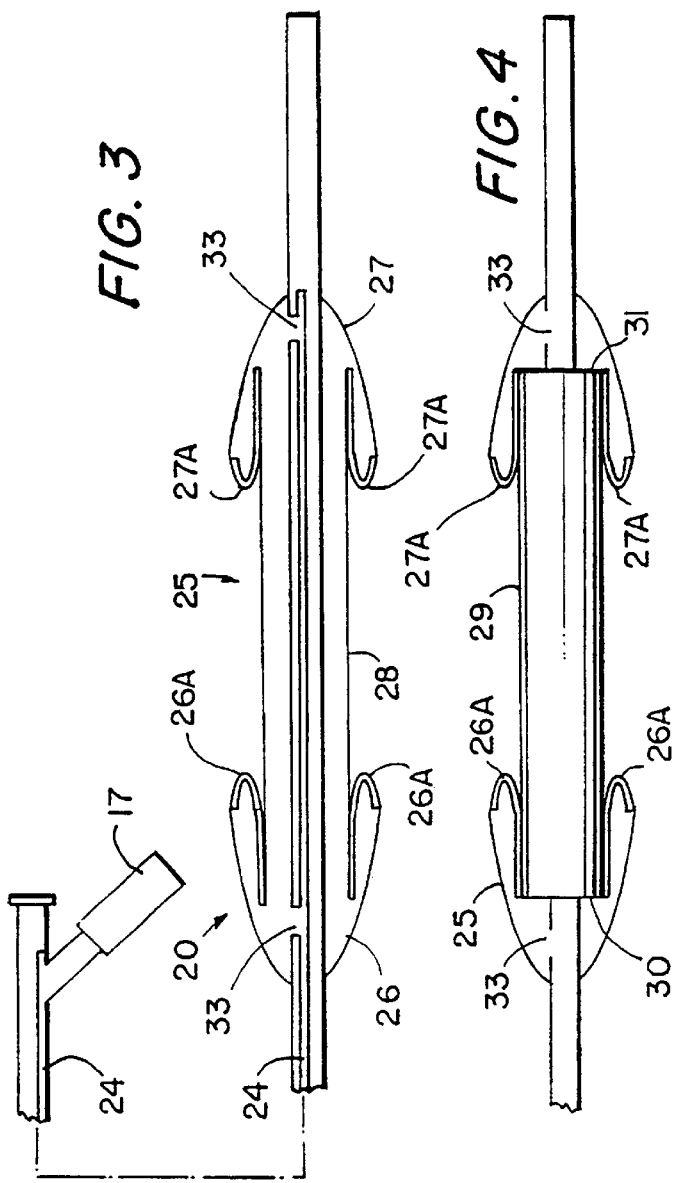

STENT DELIVERY SYSTEM

This application claims the benefit of Ser. No. 60/102,529, filed Sep. 30, 1998.

FIELD OF THE INVENTION

This invention relates to a stent delivery system. More particularly, this invention relates to a balloon sheath for sheathless delivery of balloon-expandable stents.

BACKGROUND OF THE INVENTION

The concept of implantable stents for use in medical applications has been known for many years, and a primary means of delivering an unexpanded stent into a body vessel or cavity is by use of a balloon catheter. In practice, the stent is mounted at the distal end of the catheter over an inflatable membrane (balloon) and is carried to a remote treatment area by guiding the catheter through appropriate corporeal vessels. Positioning of the catheter is tracked by fluoroscopic, radiographic or other suitable means, and, once the stent is properly positioned in a vessel or organ, the balloon is inflated, thereby forcing the stent outwardly into a fully expanded position.

Balloon-expandable stents have become a mainstay of vascular and non-vascular interventional procedures. All designs of balloon-expandable stents require mounting of the stent on a balloon, and some involve placement of a sheath over the balloon. Thus, balloon expandable stent delivery systems come in either sheathed or sheathless designs. FIGS. 1 and 2 illustrate a common prior art sheathless balloon-expandable stent delivery system in its undeployed and deployed states, respectively.

The sheath used in balloon-expandable stent delivery systems provides protection for the stent, prevents it from being dislodged from the balloon catheter, and also provides a smooth surface for reduction of friction between the stent and corporeal vessels. The sheath, however, increases the bulk and diameter of the stent delivery system and decreases its flexibility and trackability.

Sheathless stent delivery systems, on the other hand, have lower profiles and are more trackable. However, there is substantial friction between the irregular stent surface and corporeal vessel walls, particularly in areas of calcification. The uncovered stent may thus become damaged during placement due to contact with the guide catheter or corporeal vessel walls. The stent may also become dislodged from the balloon catheter, resulting in significant patient complications. In addition, the friction between the stent and corporeal vessel walls may cause damage to the vessel walls.

It is desirable to provide a delivery system that possesses the low profile and trackability of a sheathless system as well as the protection and decreased friction of a sheathed system.

OBJECTS OF THE INVENTION

It is, therefore, an object of the present invention to improved devices for implanting balloon-expandable stents.

It is another object of the present invention to enable more accurate positioning of a balloon-expandable stent during the implantation procedure.

It is a further object of the present invention to prevent the loss of a balloon-expandable stent from the insertion catheter during the implantation procedure.

It is yet another object of the present invention to provide a smooth surface for reduction of friction between a sheathless balloon-expandable stent delivery system and corporeal vessel walls.

It is yet another object of the present invention to increase the flexibility and trackability of a sheathless balloon-expandable stent delivery system.

These and other objects of the invention will become more apparent from the discussion below.

SUMMARY OF THE INVENTION

In accordance with these and other objects of the present invention, a sheathless balloon-expandable stent delivery system is provided. The ends of the balloon of the stent delivery system are invaginated and folded over onto the balloon itself such that, when a stent is mounted on the balloon, the balloon ends fold over the ends of the stent, thus covering the ends of the stent and protecting the stent and stent ends in the same manner that a sheath would. Dependent upon the length of the stent and the size and design of the balloon, the folded-over ends could cover the terminal portions of the stent or could reach to the middle of the stent and cover virtually the entire stent. When the balloon is inflated to deploy the stent, the balloon ends move substantially longitudinally as they inflate and uncover the stent.

Balloon inflation ports in the balloon catheter could optionally be positioned or configured to preferentially direct the inflation fluid into the balloon ends/invaginations to assure their inflation before the inflation of the body of the balloon. Because the stent will be in a crimped or undeployed state positioned circumferentially around the middle portion of the balloon, the pressure and radial force required to inflate the body of the balloon will be much greater than the pressure or force required to inflate the unrestricted balloon ends. The balloon ends will thus expand and move substantially longitudinally away from the ends of the stent before the stent expands so as not to become trapped between the stent and an organ or corporeal vessel wall.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIG. 1 illustrates a cross-sectional view of a common prior art sheathless balloon-expandable stent delivery system in its undeployed state;

FIG. 2 illustrates a cross-sectional view of a common prior art sheathless balloon-expandable stent delivery system in its deployed state;

FIG. 3 illustrates a cross-sectional view of the balloon of the balloon-expandable stent delivery system of the present invention in its undeployed state without a stent mounted thereon, with the balloon ends invaginated and folded over onto the ends of the balloon;

FIG. 4 illustrates a cross-sectional view of the balloon-expandable stent delivery system of the present invention in its undeployed state with a stent mounted thereon and with the balloon ends invaginated and folded over the ends of the stent; and FIG. 5 illustrates a cross-sectional view of the balloon-expandable stent delivery system of the present invention in its deployed state with a stent mounted thereon.

DESCRIPTION OF THE INVENTION

The present invention will be described with reference to a balloon-expandable stent having a design such as is well known and widely used within the industry. As illustrated in FIG. 1 (prior art), a balloon-expandable stent delivery system, also known as a balloon catheter, generally designated 10, is cross-sectionally shown as being guided into a blood vessel 11 having plaque 12. Balloon catheter 10 has a longitudinally extending hollow outer tubular member 13 containing two or more lumens through which one or more inner hollow tubular members or guidewires (not shown) can pass. The inner tubular members or guidewires pass through guidewire lumen 14 and extend distally of the distal end 13A of outer tubular member 13. Typically, a guidewire (not shown) is passed through guidewire lumen 14 into the blood vessel 11, over which catheter 10 is guided into a desired location within an organ or corporeal vessel. A longitudinally extending inflatable balloon 15 is bonded to the outer surface 13B of tubular member 13. Fluid under pressure is delivered from an inflator 17 proximal to balloon 15 via inflation lumen 18, causing balloon 15 to inflate and expand radially. When in an uninflated state, balloon 15 lies flaccidly against the outer surface 13B of tubular member 13.

An undeployed stent 16 that is to be implanted within corporeal vessel 11 is mounted upon tubular member 13 circumferentially around balloon 15. Stent 16 is typically a cylindrical member, which, when in an undeployed (unexpanded) state, as shown in FIG. 1, will expand radially when a predetermined radial force is applied thereto. The radial force is provided by inflatable balloon 15 over which stent 16 is mounted, and the delivery vehicle for the stent is typically balloon catheter 10, as discussed above. FIG. 2 shows stent 16 in its deployed (expanded) state, in which balloon 15 is inflated and stent 16 has expanded radially due to the radial force applied by inflated balloon 15.

FIG. 3 illustrates a "balloon-sheath" for a sheathless balloon-expandable stent delivery system according to the invention. As cross-sectionally shown in FIG. 3, balloon catheter 20 has a tubular member 23 comprising an inflation lumen 24, through which fluid under pressure is delivered from inflator 17. A longitudinally extending balloon 25 is bonded to the outer surface 23A of tubular member 23 such that, when in an uninflated state, balloon 25 lies flaccidly against outer surface 23A of tubular member 23. However, according to the invention, balloon 25 has sufficient material at ends 26,27 (the attachment points to tubular member 23) beyond the amount of balloon material contained in a standard balloon catheter, as shown in FIG. 1, such that this extra balloon material at ends 26,27 allows ends 2e,27 of balloon 25 to be invaginated and folded inward over the outside of balloon 25. Thus, balloon ends 26,27 form invaginated end portions 26A, 27A that can be folded inward, over the outside of balloon 25, toward the central region 28 of balloon 25.

When stent 29 is mounted onto balloon 25, as shown in FIG. 4, balloon ends 26,27 are folded inward over the ends of stent 29 such that balloon ends 26,27 form invaginated end portions 26A, 27A that extend over edges and terminal portions 30,31 of stent 29 and extend inward toward the central region of stent 29. Thus, when balloon catheter 20 is inserted into and guided through corporeal vessel 11, invaginated end portions 26A, 27A of balloon 25 cover edges and terminal portions 30,31 of stent 29 and protect in the same manner as a sheath. Invaginated end portions 26A, 27A of balloon 25 thereby provide protection for stent 29 and prevent it from being dislodged from balloon catheter 20 during insertion and also provide a smooth surface for reduction of friction between stent 29 and an organ or corporeal vessel. Dependent upon the length of stent 29 and the size and design of balloon 25, folded over (invaginated) end portions 26A, 27A could cover just the edges and terminal portions 30,31 of stent 29. Alternatively, folded over (invaginated) end portions 26A, 27A could reach to the middle of stent 29 and cover stent 29 substantially entirely.

Balloon 25 is in fluid communication with inflation lumen 24. Once balloon catheter 20 has been maneuvered such that stent 29 is in proper position within corporal vessel 11 relative to plaque 12, fluid under pressure is delivered to balloon 25 from inflator 17 proximal to balloon 25, causing balloon 25 to inflate and expand radially. When balloon 25 is inflated to deploy stent 29, ends 26,27 of balloon 25 inflate and invaginated end portions 26A, 27A unfold and move substantially longitudinally, thereby uncovering stent 29 and its edges and terminal portions 30,31. The balloon material at ends 26,27 discussed above inflates with the rest of balloon 25 to allow balloon 25 to have a full diameter along its entire inflated length, including at ends 26,27, as shown in FIG. 5. After stent 29 is deployed, balloon 25 is deflated and removed from vessel 11.

However, should central portion 28 of balloon 25 inflate and expand outward before invaginated end portions 26A, 27A do, stent 29 may become misaligned with plaque 12 in vessel 11. Thus, to assure inflation of invaginated end portions 26A, 27A before inflation of central portion 28 of balloon 25, the balloon inflation ports 33 in outer shaft 23 of balloon catheter 20 are preferentially positioned to direct the inflation fluid into the balloon ends 26,27 and, more particularly, into invaginated end portions 26A, 27A. Then, ends 26,27 of balloon 25 are expanded before central portion 28 of balloon 25 such that stent 29 remains centered on balloon 25 and in alignment with plaque 12 in vessel 11.

In addition, because invaginated ends portions 26a, 27a may tend to become trapped between stent 29 and the walls of vessel 11 (or an organ), the uneven expansion of balloon 25 will perhaps more significantly aid in this regard. AS shown in FIG. 4, stent 29 will be crimped or held on the body of balloon 25 by virtue of invaginated ends portions 26A, 27A and, therefore, the pressure and wall tension required to inflate central portion 28 of balloon 25 will be much greater than the pressure required to inflate balloon ends 26,27, which are unrestricted. Accordingly, the preferential direction of inflating fluid into the balloon ends 26,27 to cause the expansion of invaginated end portions 26A, 27A before central portion 28 of balloon 25 allows invaginated end portions 26A, 27A to move away from edges 30,31 of stent 29 before stent 29 expands. Thus, invaginated end portions 26A, 27A will not become trapped between stent 29 and the wall of vessel 11.

The stent delivery system is comprised of polyethylene, polypropylene and other polymers or co-polymers that are typically used in medical devices of this type. Moreover, it is believed that known production techniques would be employed by those skilled in the art.

Thus, a sheathless balloon expandable stent delivery system is provided. One skilled in the art will appreciate that the present invention can be practiced by other than the described embodiments, which are provided for purposes of illustration and not limitation, and that the present invention is limited only by the claims that follow.

I claim:

1. A balloon expandable stent delivery apparatus for implanting a stent within a corporeal vessel or organ, said apparatus comprising:

a catheter having an elongated tubular member with an outer surface, proximal and distal ends, and at least one lumen extending therethrough, an inflatable balloon attached to the outer surface of said catheter and having two end sections and a midsection therebetween, said balloon being in fluid communication with said at least one lumen in said catheter for inflation of said balloon;

a radially expandable stent having two end sections and a midsection therebetween mounted in an unexpanded state over the midsection of said balloon between said balloon end sections; and inflation means connected to said inflation lumen for inflating said balloon from its uninflated state wherein said stent is unexpanded to its inflated state wherein said stent is expanded, wherein said ends of said balloon in its uninflated state are folded over said end sections of said stent in its unexpanded state such that said stent end sections lie between said balloon ends sections and said balloon midsection and are covered by said balloon end sections.

2. The apparatus of claim 1, wherein the ends of said stent do not contact said corporeal vessel or organ during movement of said delivery apparatus through said corporeal vessel or organ prior to implantation of said stent.

3. The apparatus of claim 1, wherein said ends of said balloon in its uninflated state are crimped over the ends of said stent in its unexpanded state.

4. The apparatus of claim 1, wherein said stent is self-locking such that, once expanded, it locks in said expanded position.

5. The apparatus of claim 1, wherein said ends of said balloon in its uninflated state are folded over said end sections of said stent in its unexpanded state whereby, upon inflation of said balloon, said balloon expands to approximately a full cylindrical cross section.

6. The apparatus of claim 1, wherein said ends of said balloon in its uninflated state are folded over said end sections of said stent in its unexpanded state whereby, upon inflation of said balloon, said ends sections of said balloon expand substantially longitudinally away from said end sections of said stent, thereby uncovering the end sections of said stent.

7. The apparatus of claim 1, wherein said balloon is in fluid communication with said at least one lumen for inflation of said balloon such that inflation of said balloon by said inflation means causes said two end sections of said balloon to inflate before said midsection of said balloon, whereby upon inflation of said balloon, said ends sections of said balloon expand substantially longitudinally away from said end sections of said stent, thereby uncovering the end sections of said stent.

8. A delivery apparatus for implanting a medical device within a corporeal vessel or organ comprising:

a tubular member having an elongated body with an outer surface, proximal and distal ends, and at least one lumen extending therethrough, an inflatable member attached to the outer surface of said tubular member body and having two end sections and a midsection therebetween, said inflatable member being in fluid communication with said at least one lumen for inflation thereof;

an implantable, radially-expandable medical device having two end sections and a midsection therebetween mounted in an unexpanded state over the midsection of said inflatable member; and inflation means connected to said lumen for inflating said inflatable member from its uninflated state wherein said medical device is unexpanded to its inflated state wherein said medical device is expanded, wherein said ends of said inflatable member in its uninflated state are folded over said end sections of said medical device in its unexpanded state such that said medical device ends sections lie between said inflatable member ends sections and said inflatable member midsection and are covered by said inflatable member end sections.

9. The apparatus of claim 8, wherein the ends of said medical device do not contact said corporeal vessel or organ during movement of said delivery apparatus through said vessel or organ prior to implantation of said medical device.

10. The apparatus of claim 8, wherein said medical device is a stent.

11. The apparatus of claim 9, wherein said tubular member is a catheter, and said inflatable member is a balloon.

12. The apparatus of claim 9, wherein said ends of said inflatable member in its uninflated state are folded over said end sections of said medical device in its unexpanded state whereby, upon inflation of said inflatable member, said ends sections of said inflatable member expand substantially longitudinally away from said end sections of said medical device, thereby uncovering the end sections of said medical device.

13. The apparatus of claim 9, wherein said inflatable member is in fluid communication with said at least one lumen for inflation of said inflatable member such that inflation of said inflatable member by said inflation means causes said two end sections of said inflatable member to inflate before said midsection of said inflatable member, whereby upon inflation of said inflatable member, said ends sections of said inflatable member expand substantially longitudinally away from said end sections of said medical device, thereby uncovering the end sections of said medical device.

14. In an balloon expandable stent delivery apparatus, said apparatus having a catheter with an elongated body, an outer surface, proximal and distal ends, and at least one lumen extending therethrough; an inflatable balloon attached to the outside surface of said catheter body and having two end sections and a midsection therebetween, said balloon being in fluid communication with said at least one lumen for inflation of said balloon; a radially expandable stent having two end sections and a midsection therebetween and mounted in an unexpanded state over the midsection of said balloon between said balloon end sections, the improvement comprising said ends of said balloon in its uninflated state being folded over said end sections of said stent in its unexpanded state such that said stent ends sections lie between said balloon ends sections and said balloon midsection and are covered by said balloon end sections.

15. The apparatus of claim 14, wherein said ends of said balloon in its uninflated state are crimped or folded over the ends of said stent in its unexpanded state.

16. The apparatus of claim 15, wherein said balloon is in fluid communication with said at least one lumen for inflation of said balloon such that inflation of said balloon causes said two end sections of said balloon to inflate before said midsection of said balloon, whereby upon inflation of said balloon, said ends sections of said balloon expand outward away from said end sections of said stent, thereby uncovering the end sections of said stent.

17. A method for implanting a stent within a body vessel or organ, comprising the steps of:

forming a catheter having an elongated body with an outer surface, proximal and distal ends, and at least one lumen extending therethrough, attaching a balloon having two end sections and a midsection therebetween along the outside surface of said catheter body such that a first end of said balloon is attached proximally along said catheter body and a second end of said balloon is attached distally along said catheter body, whereby said balloon is in fluid communication with said at least one lumen for inflation of said balloon;

connecting inflation means to said lumen for inflating said balloon from its uninflated state to its inflated state;

mounting a radially-expandable stent having two end sections and a midsection therebetween in an unexpanded state over the midsection of said balloon between said balloon end sections;

folding said ends of said balloon in its uninflated state over said end sections of said stent in its unexpanded state such that said stent end sections lie between said balloon end sections and said balloon midsection and are covered by said balloon end sections;

inserting said balloon-bearing catheter distally into a patient's body vessel or organ so that said stent is positioned at a desired location, whereby said ends of said stent do not contact said body vessel or organ during movement of said catheter through said body vessel or organ;

causing said balloon to be inflated and said stent to be expanded;

causing said balloon to be deflated, said stent remaining in said expanded position at said desired location; and withdrawing said balloon-bearing catheter from said patient.

18. The method of claim 17 further comprising the step of crimping or folding said ends of said balloon in its uninflated state over the ends of said stent in its unexpanded state.

19. The method of claim 17, wherein said step of attaching a balloon further comprises attaching a balloon whose ends in said balloon's uninflated state are folded over said end sections of said stent in its unexpanded state whereby, upon inflation of said balloon, said balloon expands to approximately a full cylindrical cross section.

20. The method of claim 17, wherein said step of attaching a balloon further comprises attaching a balloon whose ends in said balloon's uninflated state are folded over said end sections of said stent in its unexpanded state whereby, upon inflation of said balloon, said ends sections of said balloon expand substantially longitudinally away from said end sections of said stent, thereby uncovering the end sections of said stent.

21. The method of claim 17, further comprising the step of the step of causing said balloon to be in fluid communication with said at least one lumen such that inflation of said balloon causes said two end sections of said balloon to inflate before said midsection of said balloon, whereby said step of causing said balloon to be inflated further comprises causing said two end sections of said balloon to inflate before said midsection of said balloon such that said ends sections of said balloon expand outward away from said end sections of said stent, thereby uncovering the end sections of said stent.

22. A balloon expandable stent delivery apparatus for implanting a stent within a corporeal vessel or organ, said apparatus comprising:

a catheter having an elongated tubular member with an outer surface, proximal and distal ends, and at least one lumen extending therethrough, an inflatable balloon attached to the outer surface of said catheter and having two end sections and a midsection therebetween, said end sections and said midsection being inflatable, said balloon being in fluid communication with said at least one lumen in said catheter for inflation of said balloon;

a radially expandable stent having two end sections and a midsection therebetween mounted in an unexpanded state over the midsection of said balloon between said balloon end sections; and inflation means connected to said inflation lumen for inflating said balloon from its uninflated state wherein said stent is unexpanded to its inflated state wherein said stent is expanded, wherein said ends of said balloon in its uninflated state are folded over said end sections of said stent in its unexpanded state such that said stent end sections lie between said balloon ends sections and said balloon midsection and are covered by said balloon end sections and whereby, upon inflation of said balloon, said ends sections of said balloon inflate such that said balloon is not between said stent in its expanded state and the corporeal vessel.

* * * * *